(12) United States Patent
Knaus et al.

(10) Patent No.: US 9,315,774 B2
(45) Date of Patent: Apr. 19, 2016

(54) DEVICE FOR THE ASEPTIC EXPANSION OF CELLS

(71) Applicant: CELL MEDICA LIMITED, London (GB)

(72) Inventors: Rainer Ludwig Knaus, London (GB); Gavin Holms, London (GB); Katy Rebecca Newton, London (GB); Tina Lesley Crombie, London (GB); Andrew Roy MacLeod Provan, Stockport (GB)

(73) Assignee: Cell Medica Limited, London (GB)

( * ) Notice: Subject to any disclaimer, the term of this patent is extended or adjusted under 35 U.S.C. 154(b) by 0 days.

(21) Appl. No.: 14/353,170

(22) PCT Filed: Oct. 19, 2012

(86) PCT No.: PCT/GB2012/052587
§ 371 (c)(1),
(2) Date: Apr. 21, 2014

(87) PCT Pub. No.: WO2013/057500
PCT Pub. Date: Apr. 25, 2013

(65) Prior Publication Data
US 2014/0273077 A1 Sep. 18, 2014

Related U.S. Application Data

(60) Provisional application No. 61/550,246, filed on Oct. 21, 2011.

(51) Int. Cl.
*C12M 1/12* (2006.01)
*C12N 5/0783* (2010.01)
*C12M 1/24* (2006.01)
(Continued)

(52) U.S. Cl.
CPC .......... *C12N 5/0636* (2013.01); *C12M 23/08* (2013.01); *C12M 23/24* (2013.01); *C12M 25/02* (2013.01); *C12M 29/20* (2013.01); *C12M 37/02* (2013.01)

(58) Field of Classification Search
CPC ...... C12M 23/08; C12M 23/24; C12M 25/02; C12M 29/20; C12M 37/02; C12N 5/0636
USPC ...................................................... 435/297.5
See application file for complete search history.

(56) References Cited

U.S. PATENT DOCUMENTS 5,693,537 A    12/1997  Wilson et al.
6,027,694 A *  2/2000  Boulton et al. ............ 435/288.4
(Continued)

FOREIGN PATENT DOCUMENTS

EP    0 307 048 A2    3/1989
WO    96/40876        12/1996
WO    2005/035728 A2   4/2005

OTHER PUBLICATIONS

International Search Report, dated Dec. 17, 2012, and Written Opinion issued in International Application No. PCT/GB2012/052587.
(Continued)

*Primary Examiner* — Nathan Bowers
*Assistant Examiner* — Timothy Barlow
(74) *Attorney, Agent, or Firm* — Ronald J. Kamis; Debora Plehn-Dujowich; Prismatic Law Group, PLLC (57) ABSTRACT

A closed system suitable for the aseptic culturing therapeutic cells comprises a vessel comprising: a gas permeable portion suitable for supporting cell growth and allowing delivery of gases to the cells during culturing, a vent comprising a conduit having an exterior orifice and an interior orifice spaced apart therefrom, the vent extending from the exterior of the system into the internal volume of the vessel and terminating therein with the interior orifice, wherein the interior orifice is arranged such that during filling and emptying of liquid medium it is not susceptible to blockage by liquid, the exterior orifice is adapted to connect to an aseptic filter thereby allowing passage of gases through the filter into the vessel or out of the vessel, as required to achieve the entry and exit of fluids and cells into the vessel, a port or ports adapted to allow introduction of fluids and cells aseptically into the vessel, and a port or ports adapted to allow fluids to exit the system without exposing the system to the external environment and adapted such that cells grown therein may exit the system under gravity when the system is orientated to put the cells in fluid communication with the exit port and the latter is opened. The present system facilitates the aseptic manufacturing of cells for use in therapy, without the need for a clean-room environment because no open processing steps are required.

21 Claims, 9 Drawing Sheets

(51) Int. Cl.
*C12M 1/04* (2006.01)
*C12M 1/00* (2006.01)

(56) References Cited

U.S. PATENT DOCUMENTS 6,063,618 A     5/2000  Weuster-Botz et al.
7,754,478 B2 *  7/2010  Suzuki et al. .............. 435/293.1

OTHER PUBLICATIONS

Written Opinion, dated Sep. 23, 2013, issued in International Application No. PCT/GB2012/052587.
International Preliminary Report on Patentability, dated Jan. 9, 2014, issued in International Application No. PCT/GB2012/052587.

* cited by examiner

DEVICE FOR THE ASEPTIC EXPANSION OF CELLS

CROSS-REFERENCE TO RELATED APPLICATIONS

This application is a U.S. national stage of, and claims the priority of PCT/GB2012/052587, filed on Oct. 19, 2012, which claims the benefit of priority to U.S. Provisional Application No. 61/550,246, filed on Oct. 21, 2011, the entire contents of which are fully incorporated herein by reference.

BACKGROUND OF THE INVENTION

The present disclosure relates to an optimised system for aseptically culturing cells for therapeutic applications on a commercially viable scale, methods of manufacturing said systems and methods of using the systems to manufacture cellular therapeutics.

Figure 1:
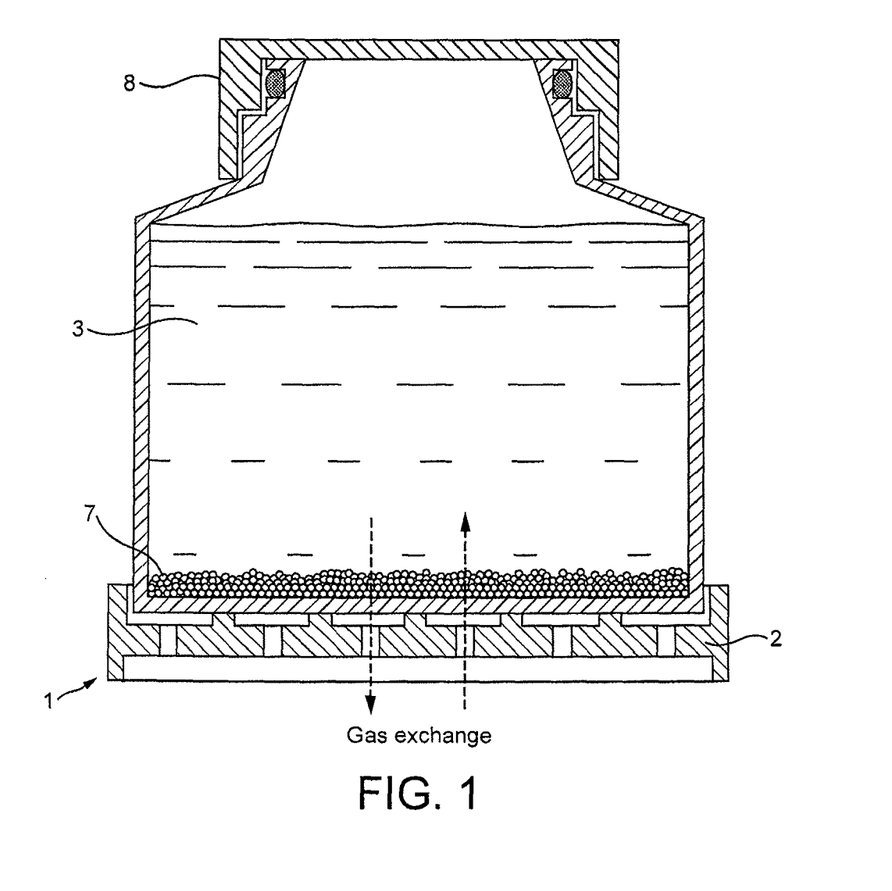
FIG. 1 shows a diagrammatic representation of the commercially available G-Rex system for cell culture available from Wilson Wolf.

WO 2005/035728 describes a system with a gas permeable portion for culturing cells. This device is available from Wilson Wolf under the brand G-Rex Technology (please see the website www.wilsonwolf.com/page/show/67596). The main benefit of the system is that it allows nutrients and gases to be provided to growing cells in a way so that the cells can be continuously grown for periods of up to 14 days without any further intervention, in particular: the gas permeable membrane allows exchange of $CO_2$ and $O_2$ and the arrangement allows large volumes of media to be employed which provides all the nutrients necessary for growth. The arrangement is shown in FIG. 1.

The main limitation of the G-Rex technology is that it is an open manufacturing system that does not allow the inoculation and harvesting of cells and addition of nutrients without exposure to the external environment. Since cellular therapeutics cannot be sterilised post production, their manufacture has to occur under aseptic conditions. Thus the "open" processing steps during which the product is exposed to the external environment have to be performed under a laminar air flow cabinet which is operated in a clean-room classified according to EU-GMP classification class B (US Fed. Std. 209e class 10,000, ISO 14644-1 class ISO7) to prevent contamination of the product with microbes and particles. Facilities with such clean-room technology, for open processing, are expensive to build, operate, maintain and monitor.

Equally important is the fact that the open operation steps require that only one product can be handled at a time in the same clean-room space to minimise the risk of cross-contamination, hence, the product throughput is limited and this manufacturing system requires multiple clean-rooms and production teams to operate in parallel to achieve high volumes of production output. For small and medium size companies as well as hospitals, the capital investment and labour costs are very significant on a per unit basis of production.

To address this problem the present inventors have provided a modified system for the culture of cells that allows aseptic manufacturing of cells for use in therapy, without the need for a clean-room environment because no open processing steps are required.

SUMMARY OF THE INVENTION

Thus the present invention provides a closed system suitable for aseptically culturing therapeutic cells comprising
i) a vessel comprising:
   a gas permeable portion suitable for supporting cell growth and allowing delivery of gases to the cells during culture, and
   at least one wall adjoined to a base, wherein said vessel defines an internal volume and said vessel is adapted to contain a requisite volume of medium to support cells during culture,
ii) a vent comprising a conduit defining an interior orifice and an exterior orifice distal therefrom in fluid communication with each other, wherein the conduit extends from the exterior of the closed system through a structural feature of the system, optionally extends into the internal volume of the vessel, and terminates in the internal volume with the interior orifice, wherein the interior orifice is located in the internal volume such that during filling and emptying of liquid media and/or cells it is not susceptible to blockage by liquid or cells,
   wherein the exterior orifice is adapted to connect to an aseptic filter thereby allowing gases to pass through the filter into the vessel or out of the vessel, as required,
iii) a port adapted to allow introduction of fluid and cells aseptically into the vessel, a port adapted to allow fluid and cells to exit the system without exposing the system to the external environment and adapted such that cells grown therein may exit the system under gravity when the system is orientated to put the cells in fluid communication with the exit port and the latter is open.

The system according to the present invention has significant benefits for the commercial manufacturing of cells for use in therapy. In particular it is flexible and adaptable, requires low capital investment into manufacturing space, and is robust and easily manufactured. It also eliminates open processing steps and therefore further reduces the risk of contamination of the product with pathogens and particles. Further, the present system is believed to meet a currently unmet need, and represents a real step forward in reducing the need for expensive clean-room facilities for the manufacture of therapeutic cells.

Advantageously, the present invention allows the transformation of existing open system technology, such as the G-Rex system, to provide a closed system that allows the inoculation and harvesting of cells and the provision of nutrients without exposure to the external environment.

Figure 7:
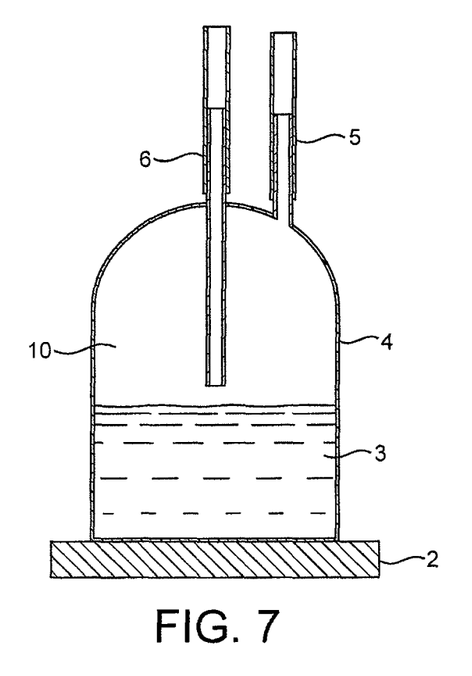
FIG. 7 is a diagrammatic representation of a bell shaped unitary vessel according to the present disclosure comprising a vent and port co-located in a wall of the unit.
Figure 8:
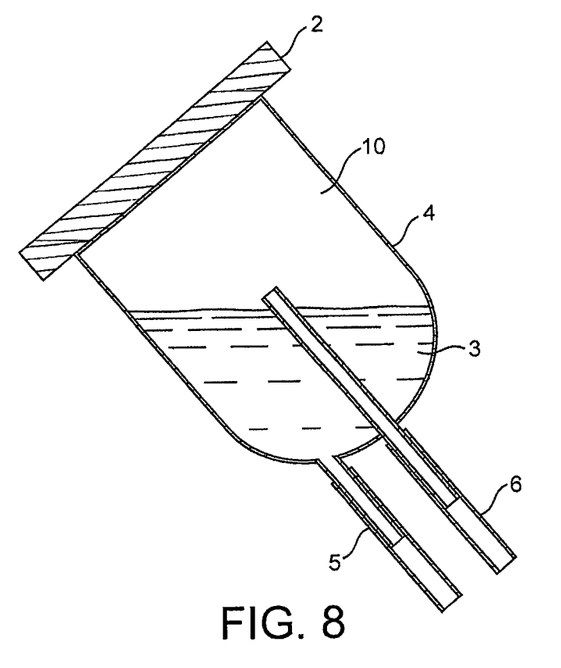
FIG. 8 is a diagrammatic representation of a bell shaped unitary vessel according to the present disclosure comprising a vent and port co-located in a wall of the unit and orientated to allow access of the media and cells to the exit port.

Alternatively, a bespoke system according to the present disclosure may be manufactured specifically for culturing cell therapeutics, for example a system shown in FIG. 7 or 8.

The present disclosure also extends to methods of manufacturing the systems described herein and also use of the systems to culture cells.

DETAILED DESCRIPTION OF THE INVENTION

A closed system as employed herein allows entry and exit of materials including liquids, cells and gases without exposure to the external environment.

A closed system according to the present disclosure can nevertheless be employed as an open system if the end user decides not follow appropriate protocols when introducing or extracting material from the system. However, the systems disclosed herein are arranged and adapted to be suitable for use as a closed system.

Culturing cells as employed herein is intended to refer to expanding and/or differentiating cells in vitro.

Cell expansion as employed herein is refers to increasing the number of the target cells in a population of cells.

WO 2005/035728 incorporated herein by reference describes how to prepare a gas permeable vessel. In one embodiment silicone gas permeable material is employed.

In one embodiment the base supports incorporates the gas permeable material.

In one embodiment the base substantially consists of gas permeable material i.e. the gas permeable material layer and the base are in fact the same entity.

In one embodiment the gas permeable layer is located in a wall or other structure feature of the vessel.

In one embodiment substantially all of the vessel is prepared from a gas permeable material, for example with sufficient structural strength to retain the contents during culturing.

In one embodiment the gas permeable membrane has a surface area of, for example 5 to 200 $cm^2$, such as 5 to 100 $cm^2$, in particular 10, 30 or 50 $cm^2$, such as 10 $cm^2$.

A base as employed herein is a structural element of the vessel.

When cells are in the process of being cultured generally the systems will be orientated (or stood) on the base, for example the base is flat or substantially flat. Even if the system is not stood on the base, to allow air to circulate, then during culturing the base may represent the lowest part of the system.

Generally during the culturing process the cells tend to settle on and be supported by the internal surface of the gas permeable layer, for example in a plane which is parallel to the plane of the base.

The base in the context of the present disclosure, for example can be understood by reference to the devices shown in FIGS. 5 to 8, which shows the base (1). Clearly the gas permeable layer in the base must have access to the environmental gases for the system to function. Thus the base may be raised above the surface on which the system is stood or located, to ensure access to the external gaseous environment.

Adjoined thereto as employed herein is intended to refer to the fact that one element is attached to another.

The vessel employed will generally be rigid or substantially rigid or resiliently deformable but not permanently deformable. However the vessel may comprise portions of flexible or deformable materials. These flexible materials may include the type of materials employed in the manufacture of infusion bags.

In one embodiment the vessel and substantially all the structural elements thereof are rigid.

The vessels and systems of the present invention may be provided in a whole range of shapes and sizes, for example derived from a cube, box, cylinder, cone or pyramid. However, usually at least one area or side of the shape will be adapted for accommodating vents, port or ports and/or other elements of the system. Pure shapes may be used but will not generally be employed because the shape will usually be adapted to provide a bespoke vessel for the intended purpose. For example a cone shape may be adapted to provide a frusto-conical shape comprising a base and curved wall and a top wall or lid. The top wall or lid may accommodate the port(s) and/or vents.

In one embodiment the vessel is associated with or comprises a re-sealable lid, wherein the vessel and the lid together form the closed system. A re-sealable lid can be illustrated by reference to FIG. 1 which shows a device comprising a screw lid, which is one type of re-sealable lid.

In one embodiment, the attachment of the lid to the vessel is by screwing the lid through thread etched in the vessel thereby allowing a seal to be created which protects the contents therein from contamination from microbes and particles in the external environment.

In one embodiment a system according to the present disclosure can be provided by modifying an existing system, for example the G-Rex unit can be modified by incorporating a vent and one or two ports, to which other components of the manufacturing system can be aseptically connected. In one embodiment the vent and port or ports are incorporated into the lid of a G-Rex system. This provides a cost-effective way of producing a closed system for culturing cell therapeutics, which can be operated outside of a laminar air flow cabinet in a clean-room classified according to EU-GMP class D (US Fed. Std. 209e class 100,000, ISO 14644-1 class ISO8) since the product is never exposed to the external environment. This greatly facilitates the aseptic manufacturing of the cellular therapeutic in conformance with regulatory requirements.

In one embodiment there is provided a lid according to the present invention for a manufacturing system or vessel according to the disclosure, such as a G-Rex system, in particular said lid comprising a vent and/or port as discussed herein or fitting to accommodate same.

In one embodiment the lid, vent and/or ports are unitary, for example moulded.

In one embodiment the lid, vent and/or ports are the same material,

In one embodiment the lid, vent and/or ports are distinct materials.

In one embodiment the lid, vent and/or ports are one material and the vessel onto which the lid is adapted to fit is the same material.

In one embodiment the lid, vent and/or ports are one material and the vessel onto which the lid is adapted to fit is a distinct material.

In one embodiment the lid, vent and/or ports are distinct materials and the vessel onto which the lid is adapted to fit is a material employed in the lid or vent/port.

In one embodiment the lid, vent and/or ports are distinct materials and the vessel onto which the lid is adapted to fit is a further distinct material.

In one embodiment the a hard synthetic material suitable for use in aseptic manufacturing as described herein, such as polycarbonate, is employed to manufacture one or more of the above components.

It may be advantageous from a GLP and regulatory perspective for the vessel, lid, vents and ports to be the same material.

In one embodiment the vessel is unitary in nature in that it defines a complete unit without a removable or re-sealable element, such as a lid. Unitary vessels may, for example be moulded in one piece but unitary as employed herein is not a reference to how the vessel is made but rather is a description of the function of the vessel and in particular that no additional structural elements, such as a lid, are required to seal the vessel.

In one embodiment there is provided a bell arrangement (FIGS. 7 and 8) wherein a structural feature opposing the base provides a concave surface in the interior volume. Shapes such as bells are advantageous because the number of internal corners in the internal volume are minimised which may maximise the recovery of cells possible. The present disclosure also extends to alternative shapes which are suitable for performing this function, in particular wherein the locations capable of trapping cells are minimised by using "rounded surfaces".

Thus in one embodiment the vessel is arranged to funnel cells to the exit port when the system is situated in the appropriate orientation. In one embodiment the internal shape is adapted to facilitate drainage from an exit port when appropriately orientated.

The systems according to the present disclosure are arranged to allow removal of liquid and cells under gravity, when arranged in the required orientation. Removing the cells under gravity is advantageous because it is simple, efficient and cost-effective. Nevertheless this process may be augmented by employing a vacuum, increasing the internal pressure of the system (referred to herein as overpressure) or pumping (such as a peristaltic pump). These technologies are well known and may be employed in combination with the system by attachment of the pump, vacuum or gas input to create an over-pressure to a relevant port or vent, as appropriate.

If desired the liquid and cells may be removed by pumping, vacuum or over-pressure without the assistance of gravity, even though the system is designed to be suitable for removal of the liquid or cells gravity.

A structural element as employed herein is intend to refer to a base, wall, lid or other structural feature of the vessel that performs a function such as supporting, retaining shape and volume, holding or the like. A structural element does not refer to appendages to the vessel such as accessories, in particular ports, vents, gaskets and the like.

Unless the context indicates otherwise interior and internal are employed interchangeably herein.

Unless the context indicates otherwise exterior and external are employed interchangeably herein.

Interior volume and interior space are employed interchangeably herein.

In one embodiment the requisite volume of media which the vessel is adapted to contain is an amount that does not block the vent during culturing the cells and removal of the liquid and cells. In one embodiment the volume of media is 50% or less of the internal volume, such as 45%, 40%, 35%, 30%, 25%, 20% 15%, 10% or less. When the vessel is filled to this level then it may be appropriate to remove the contents under gravity.

In one embodiment the maximum requisite volume of media is 15 to 30 ml, such as about 20, 21, 22, 23, 24, 25 or 26 ml.

"Not susceptible to blockage by media and cells" as employed herein is intended to refer to the fact that the elements are arrangement to minimise access of the cells and/or media to the feature, such that it has a reduced propensity to becoming blocked such that is cannot perform its function.

In one embodiment the volume of media is 50% or more of the internal volume, such as 55%, 60%, 65%, 70%, 75%, 80%, 85%, 90% or 95%. In this embodiment the maximum requisite volume of media in a system such as the G-Rex 10 is 30 to 40 ml, such as about 31, 32, 33, 34, 35, 36, 37, 38 or 39 ml. When the vessel is filled to this level then it may be appropriate to employ a "pump" or other system described above to assist in removing the contents. The vent may be cleared of any media or cells located therein by the "pumping"/forced extraction process and thus the vent may become "blocked" if this system is emptied under gravitation forces only.

In one embodiment the ratio of the numeric values of the gas permeable area to the volume of the medium employed in the systems is in the range 1:1 to 1:5 respectively, for example 1:2, 1:3 or 1:4, such as 10 $cm^2$ gas permeable area to 20 ml volume which gives a ratio of 1:2.

The vent comprising a conduit defining an interior orifice and exterior orifice is essentially a pipe connecting the interior of the system to the exterior. This vent allows balancing of pressure during filling the vessel by allowing gases to exit. During the cell emptying process the vent allows gases to enter the internal volume to fill the void that would be created by removal of the liquid and cells, thereby allowing the free fluid communication of the liquid and cells to the external port using gravity or pressurized systems.

The vent terminates into the internal volume is intended to refer to the fact that the vent has access to the internal volume and the interior orifice may be located in a structural feature of the vessel such as a wall, provided that the vent is in fluid communication with the internal volume and that the vent is arranged such that it is generally not susceptible to blocking during harvesting of the cells, when the media and cells are less than 50% of the volume of the vessel.

Extends into the internal volume is intended to refer to part of the vent conduit protruding into the internal space.

In a preferred embodiment at least part of the vent physically extends and protrudes into the internal volume like an appendage anchored in the structural feature.

In one embodiment the portion of the vent terminating in the internal orifice does not terminate in the same plane as the structural element through which it is supported, that is to say the conduit will generally pass through an structural element in which it is supported and extends into the space defined by the internal volume, for example terminating centrally in the volume as shown in any one of FIGS. 2, 3, 5, 6, 7 and 10 to 12.

Located centrally as employed herein is intended to refer to the fact that part of the vent extends from the structural feature of the vessel in which it is housed and into the space of the internal volume and is not intended to be an absolute reference to the centre of the space per se. This feature has the benefit that during filling of the vessel with media or during harvesting of cells (in particular if the vent is co-located with the port for entry/exit) then exposure of the internal orifice to liquid is thereby minimised.

In one embodiment the vent is arranged to terminate in the volumetric centre of the internal volume of the vessel.

Volumetric centre as employed herein is intended to refer to approximately the centre of the three dimensional space defined by the internal volume.

In one embodiment the conduit of the vent extends between 5 and 35 mm, such as about 30 mm from the underside of the lid or other structural feature of the vessel or alternatively up from the base.

In one embodiment the interior orifice of the vent is arranged not to contact the media contained in the vessel during use, in particular when the media and cells are less than 50% of the volume of the vessel, such that the orifice and vent are not susceptible to being blocked by liquid or cells.

However the vent may be arranged such that it extends into the media contained in the vessel during use. The function of the vent may be facilitated by employing a liquid impermeable membrane, such as a gas permeable membrane over the internal orifice and/or employing a liquid non-return valve in the vent.

In one embodiment the vent may comprise a liquid non-return valve.

In one embodiment the internal orifice may be protected by a liquid impermeable membrane, such as a gas permeable membrane.

Optionally the vent may comprise a valve to control follow of gases, if desired.

The vent is arranged to be capable of attaching to a sterile filter such as a 0.2 micron filter that prevents airborne microbes and particles entering the internal volume of the vessel and contaminating the system. Generally the filtering device or element will be attached to the external orifice of the conduit forming the vent, as shown in FIGS. 2 to 6 and 9.

The attachment may be direct or via a coupling means, such as tubing.

In one embodiment the sterile filter is secured to the vent by a fixing means such as a leur lock.

The vent may be prepared from any suitable material and may be moulded in the structural feature that supports it i.e. integral thereto.

In one embodiment the vent may simply comprise flexible tubing extending through the structural feature that supports it.

In one embodiment the vent comprises an exterior portion extending outside the closed system which is suitable for connection to flexible tubing.

Suitable flexible tubing is available in many different forms, for example:
  a translucent tubing which contains no plasticizers, latex and vinyl acetate and is also free of animal products, or transfusion tubing, for example PVC transfusion grade tubing such as 4 mm OD PVC transfusion grade tubing.

In one embodiment the tubing is silicon.

The tubing employed is such that it can be connected aseptically to components also containing a tube using a sterile tube welder, for example available from Terumo Medical Corporation.

The vent can be located in any suitable location on the vessel including, for example in a structural feature such as a wall, the base, a lid, for example in one embodiment the vent extends through the gas permeable layer, which as described in detail above and may be located in the base of the vessel.

In one embodiment the vent is located centrally on a structural feature of the vessel, that is to say not proximal to an edge of a wall, base or lid.

In one embodiment the vent is located approximately along a central axis of the vessel, for example through the centre of a lid or wall and may extend to the centre of the internal volume. Centre as employed herein is intended to refer to approximately the midpoint of the space or feature.

Figure 6:
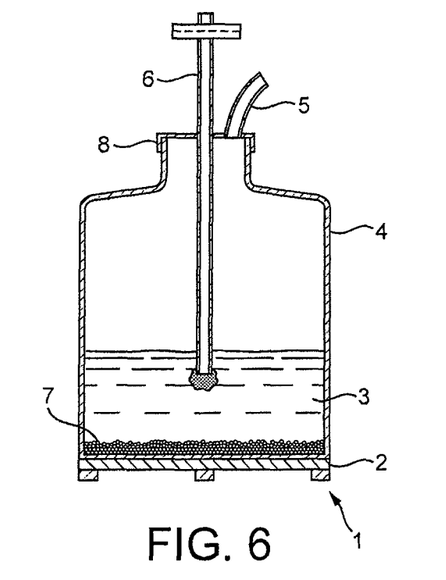
FIG. 6 is a diagrammatic representation of a vessel comprising a lid with a vent and port co-located therein, wherein the vent extends down into the media towards the gas permeable layer. The interior orifice is covered by a liquid impermeable membrane, such as a gas permeable membrane to prevent media entering the vent.

Suitable material for the port or ports when moulded include, for example the same materials as the vessel (such as thermoplastics, in particular polycarbonate). In one embodiment a moulded port or ports is/are designed such that the port or ports are suitable for connecting to tubing, for example as shown in FIG. 6 where the tubing slides onto the vent or port portion which is moulded.

In one embodiment the port or ports are provided as tubing, such as flexible tubing, extending through a structural feature of the vessel and/or system. In this embodiment the flexible tubing may need to be sealed to the structural feature by a gasket.

Tubing for use with or as a port include tubing described supra that can be used in sterile connecting devices for the aseptic connection of external components like e.g. sterile infusion bags.

The port or ports can be located in any suitable location on the vessel including for example structural features such as a wall, the base, a lid.

In one embodiment there is provided a separate entrance port and a separate exit port.

In one embodiment there is provided one port which functions as an entrance and exit port.

In one embodiment the vent is co-located with a port or ports, for example in a wall or lid.

The benefit of co-locating the vent and port or ports in a structural element opposite to the base, such as a lid or wall, is that no modifications to the vessel side wall are required. This is advantageous because vessels without features in the side walls can be placed in close proximity to each other occupying minimal space. This also allows efficient manufacture of the vent and port or ports within a single component of the vessel.

The benefit of co-locating the vent and port or ports in the lid means that no further modification of the commercially available vessel is required to convert it from an open into a closed system.

In one embodiment the port employed for cells to exit is located proximal to a structural element, such as wall, the edge of a lid or the like. The inventors have found by locating the exit port by an edge, of a wall or structural element of the vessel then a more efficient recovery of cells is obtained. An example the port located proximal to a structural feature is shown in FIGS. 2 to 12.

Having the port or ports to the side of the lid or other structural feature ensures that maximum recovery of liquid and cells is achieved. Earlier prototypes had the port in the centre of the lid, and due to the surface tension of the liquid, it was determined that 0.5 ml-0.8 ml of liquid was retained in the vessel. When the port was moved to the side, and flush with a gasket, the retention was reduced to 0.1 ml.

In addition locating the port or ports off-centre allows the vent to be located centrally, which in at least some embodiments may minimise the exposure of the vent to blockage by liquid.

Thus in one embodiment the port or ports, in particular the exit port is non-coaxial with a central axis of the internal volume of the vessel.

In the cross-sectional figures shown herein a double line represents a wall or barrier or similar which is closed. However a single line is not closure but is present to show the shape of the feature. Thus where a single line is shown at the end of a vent or port, the same is open.

Figure 2:
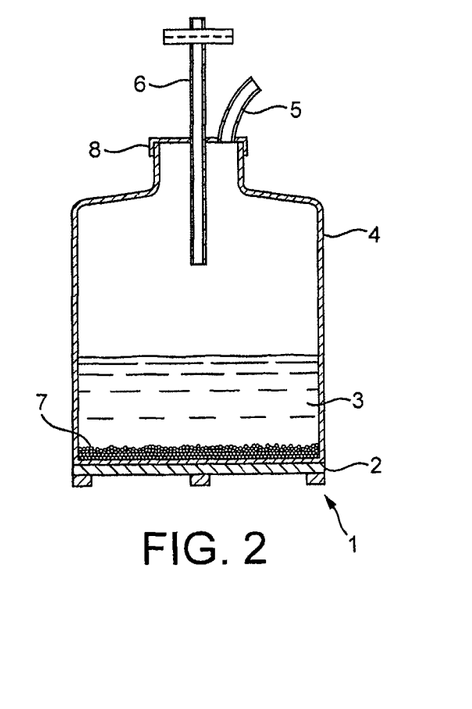
FIG. 2 is a diagrammatic representation of a vessel comprising a lid with a vent and port co-located therein.

FIG. 2 shows a gas permeable layer (2), which forms the base (1) of vessel (4), which comprises a lid (8) co-locating a vent (6) and a port (5), wherein said vent comprises a conduit defining an exterior orifice capable of supporting a sterile filter said conduit extending through the lid and extending centrally into the interior volume defined by the vessel and terminating in the interior orifice. In use the vessel contains media and cells which settle on the interior surface of the gas permeable layer.

Figure 3:
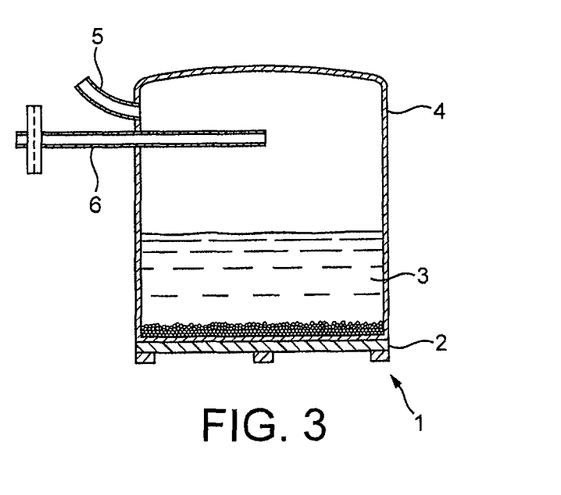
FIG. 3 is a diagrammatic representation of unitary vessel according to the present disclosure comprising a vent and port co-located in a wall of the unit.

FIG. 3 shows a similar arrangement to that of FIG. 2 but is characterised by the vessel being a single unit without a re-sealable lid. The port (5) and vent (6) are co-located in a wall (a structural element) of the vessel. The conduit of the vent extends as a protrusion into the internal volume of the vessel.

Figure 4:
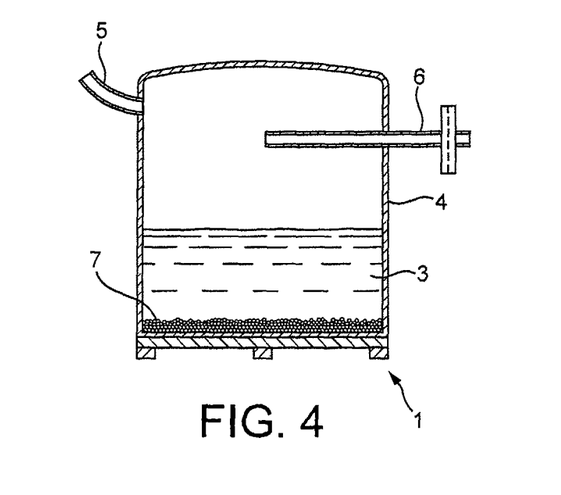
FIG. 4 is a diagrammatic representation of a unitary vessel according to the present disclosure comprising a vent and a port located opposing each other.

FIG. 4 shows a similar arrangement to FIG. 3 but wherein the port (5) and vent (6) are arranged to oppose each other.

Figure 5:
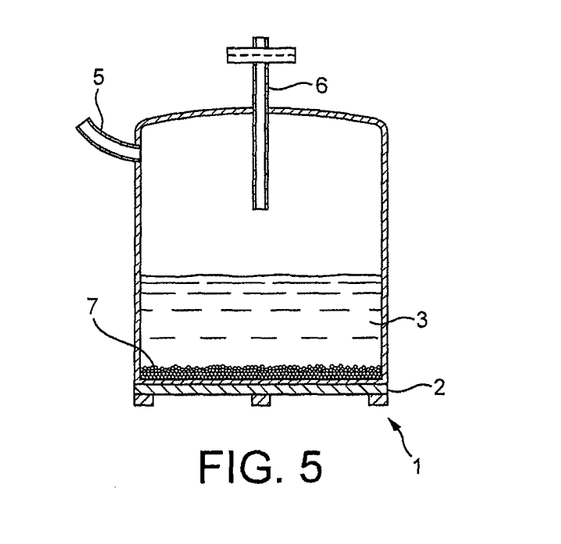
FIG. 5 is a diagrammatic representation of a unitary vessel of the represent disclosure wherein the vent and port are arranged perpendicular relative to each other.

FIG. 5 shows a similar arrangement to FIGS. 3 and 4 but wherein the port (5) and the vent (6) are arranged perpendicular to each other.

FIG. 6 shows a gas permeable layer (2), which forms the base (1) of vessel (4), which comprises a lid (8) co-locating a vent (6) and a port (5), wherein said vent comprises a conduit defining an exterior orifice capable of supporting a sterile filter said conduit extending through the lid and extending centrally into the interior volume, defined by the vessel, towards the base and into the media (3). The interior orifice is protected by a gas permeable membrane (9) which prevents blockage of the vent by liquid.

FIG. 7 shows a unitary bell shaped vessel (4) arranged with the port (5) (which has a dual function of the entrance and exit port) and the vent (6) co-located in a structural feature of the vessel opposing the base comprising a gas permeable layer. In this Figure the vent (6) and port (5) are shown with the exterior portions connected to flexible tubing.

FIG. 8 shows a system of FIG. 7 orientated to put the liquid media and cells in communication with the exit port (5), wherein the cells may exit the port under gravity. The dimensions of the Figure herein are by way of example only and are not intended to be limiting.

Sterile containers, such as infusion bags, containing materials such as a media and/or cells can be welded to an entrance port or tubing connected thereto using known technology to introduce media aseptically into the system. This is illustrated diagrammatically in FIG. 9. Sterile welding techniques and technology are well known in the industry and will not be discussed further here.

Figure 9:
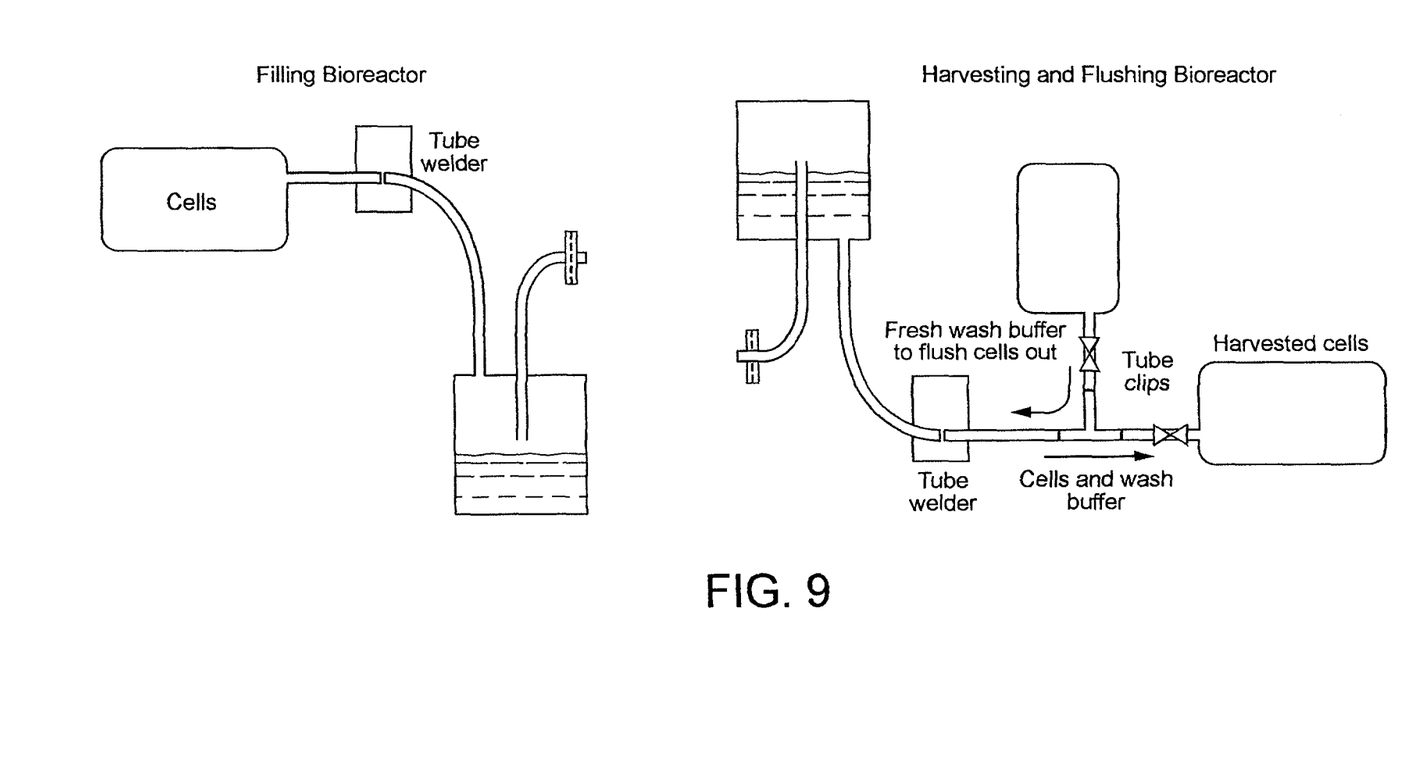
FIG. 9 is a diagrammatic representation of how a system according to the disclosure can be filled and harvested.
Figure 10:
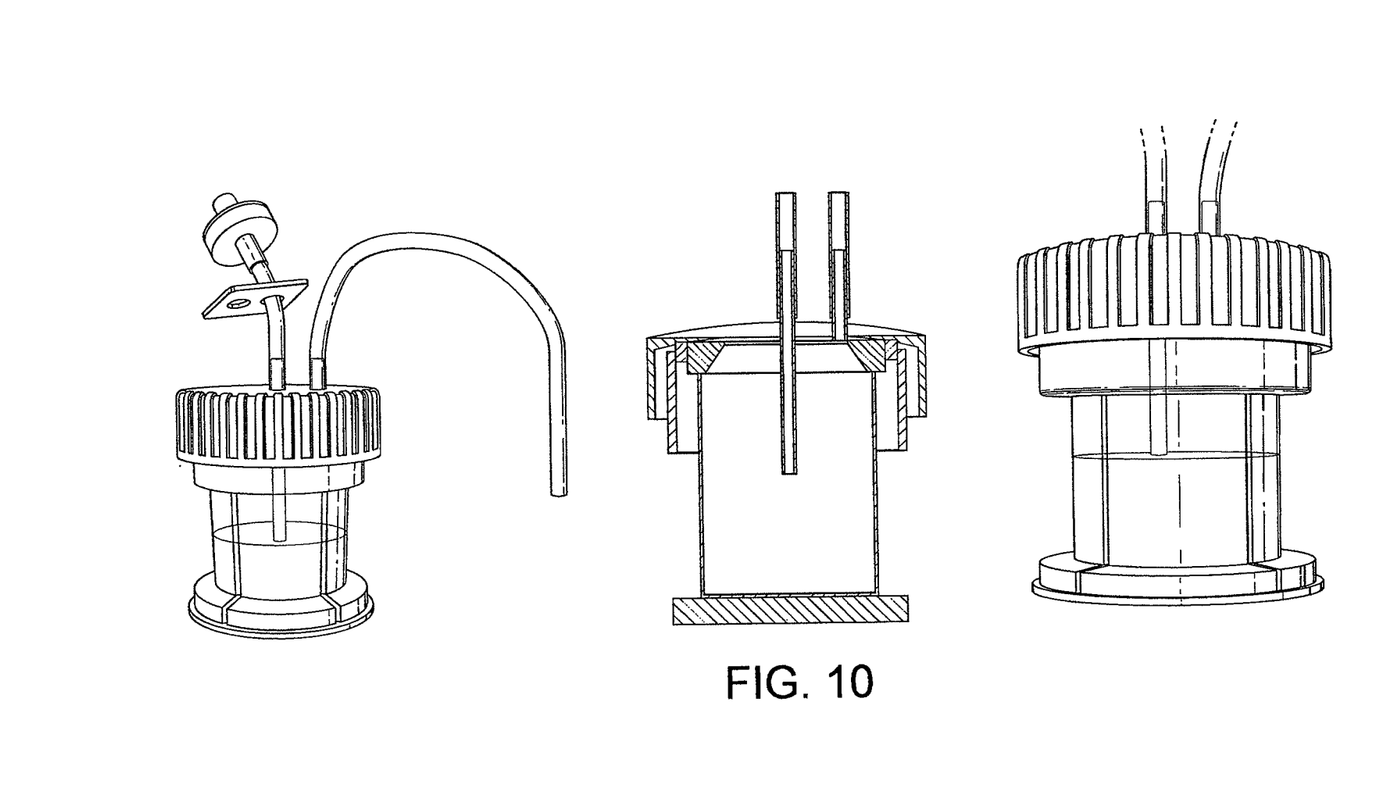
FIG. 10 is a diagrammatic representation of a system according to the present disclosure FIG. 11 are detailed drawings of a system as shown in FIG. 10
Figure 11:
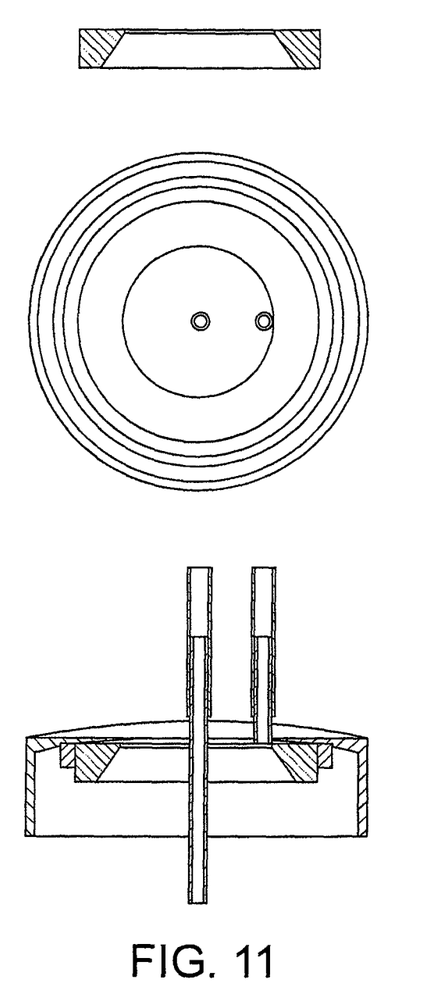
Figure 12:
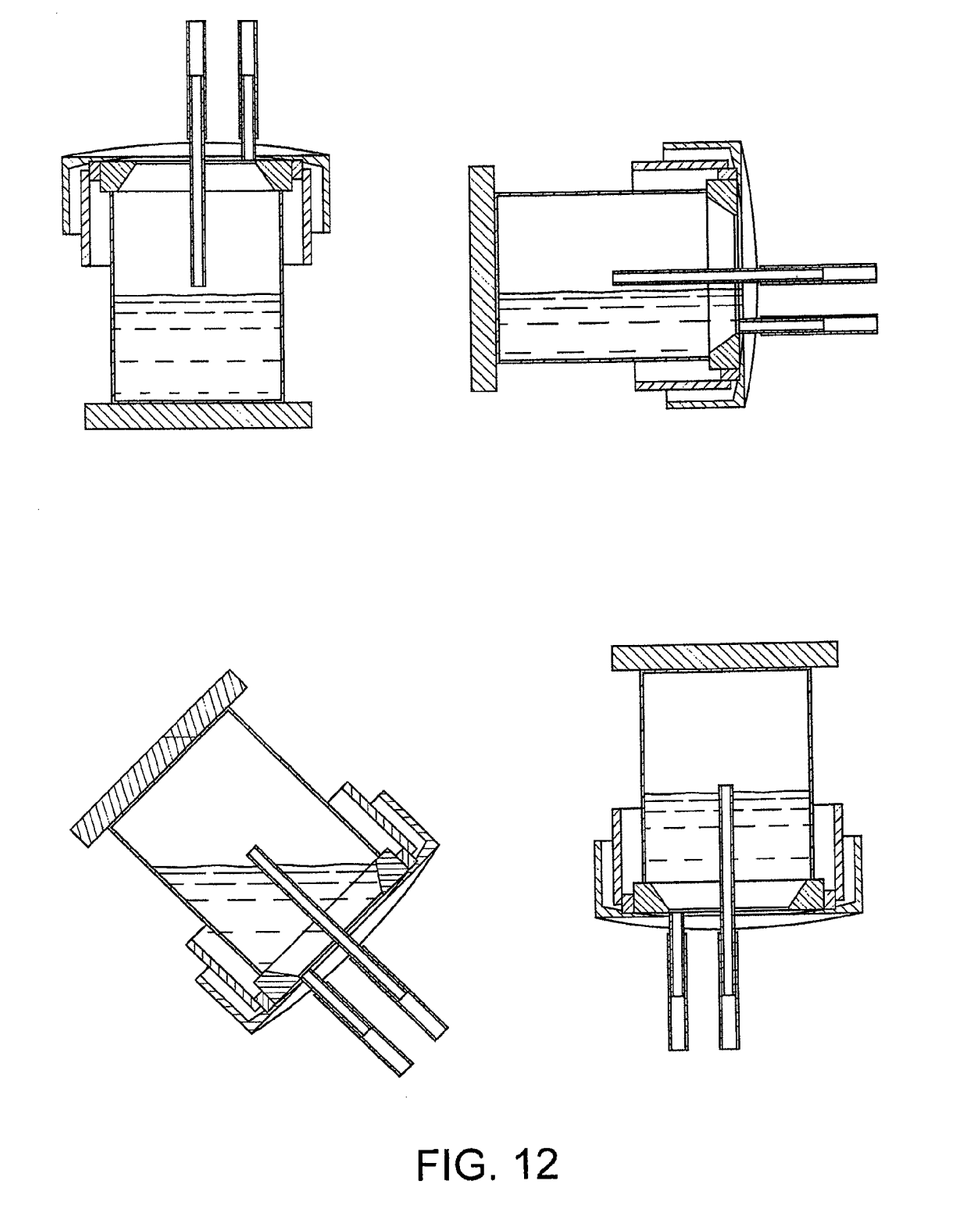
FIG. 12 is a diagrammatic representation of how to orientate the system to harvest cells cultured therein.

Similarly empty containers such as sterile infusion bags can be welded onto an exit port, or tubing connected thereto, to remove the cells from the vessel aseptically, also illustrated in FIG. 9.

Both of these methods of introducing and removing materials from the system aseptically are very convenient, robust and practical.

Allowing cells to be removed (harvested) under gravity by changing the orientation of the vessel by 10 to 350 degrees, for example 45 degrees or greater such as 90 or 180 degrees is very easy and efficient because it does not require specialised equipment and needs minimal space and expertise.

In one embodiment the exit port does not extend above a structural feature in which it is situated into the internal volume more than 0.15 mm. The later ensures maximum recovery of cells.

The port or ports may be fitted with a valve and/or membrane or the like to control flow of materials therethrough.

Suitable gaskets and seals may be required depending on the exact construction of the system.

A suitable material for manufacturing the vessel and structural elements thereof will generally be required to be compliant with one or more of the standards: EU Food Approval: EU Directive 2002/72/EC; USP <88>, biological reactivity test in vivo, class VI; USP <87>, biological reactivity test in vitro; USP <661>, physicochemical test-plastics; EP monograph 3.2.2, plastic containers & closures for pharmaceutical use; Biological tests according to ISO 10993—external communicating devices; for indirect blood contact for a prolonged period.

In one embodiment the vessel and/or structural elements of the systems are manufactured from a suitable thermoplastic such as polycarbonate.

The ports and vents may be incorporated into the system by thermal soldering, especially when a closed system is being created from a commercially available product, such as G-Rex.

In one embodiment a modified lid will be moulded in one piece with appropriate connections for tubes and/or filter, which will be attached afterward.

In one embodiment the features and structural functionality, such as ports and vents, will be created when moulding the vessel.

Structural functionality as employed herein is intended to refer to features which perform a function, for example as a vent or port and/or which is suitable for attaching accessories to, such as tubing or the like.

The systems according to the disclosure may be gamma irradiated for sterilisation.

Generally the system will be delivered to end users in a sealed bag in a sterile form, for example along with a certificate of sterility. A system in this form will generally have a shelf-life of about 1 year or more.

There is also provided a process of manufacturing a system according to the present disclosure comprising the step of moulding the vessel, and optionally fitting the ports and vents thereto.

In one embodiment the holes to accommodate a vent and/or ports are created by thermal probes rather than by drilling, thereby minimising the amount of contamination generated and ensuring the final product is suitable for use to prepare a therapeutic product.

In one embodiment further components such as gaskets and/or valves and/or filters are fitted in the manufacturing process.

In one embodiment the manufacturing process comprises the further step of sterilising the system, for example using gamma irradiation and aseptically sealing the unit in one or multiple bags or containers.

In one embodiment one or more steps of the manufacturing process are performed in a clean-room complying with standards to EU-GMP class D (US Fed, Std. 209e class 100,000, ISO 14644-1 class ISO8). In one embodiment each system together with filters, gaskets, tubes and connections and before sterilisation the assembled system will be subject to a pressure hold test with compressed air according to methods known to those skilled in the art, for example pressure testing of 0.5 bar±0.05 bar for greater than 2 mins. During this time, the pressure will not drop from its recorded start value by less than 0.05 bar.

In one embodiment there is provided a method of modifying an existing cell-culture system to provide a closed system according to the invention. The modification may employ one or more of the manufacturing steps defined above.

In one embodiment a vessel according to the disclosure, such as a modified G-Rex vessel and/or a vessel with a gas permeable membrane of about 10 cm$^2$ will typically be filled to 10 to 25 ml final volume with cells and culture medium, and will be incubated at 37° C. until the cells are ready for harvesting. Having this the vessel may be filled with up to 40 mls as discussed above.

Thus a method of introducing cells aseptically to a closed system according to the disclosure followed by incubating the cells at an appropriate temperature and for an appropriate period is provided.

In a further aspect, a method of aseptically harvesting therapeutic cells from a closed system according to the disclosure by aseptically joining a receptacle to an exit port of the system and harvesting the cells into receptacle under gravity is provided.

In a further aspect, a method of aseptically harvesting therapeutic cells from a closed system according to the disclosure by aseptically joining a receptacle to an exit port of the system and harvesting the cells into receptacle employing a pump is provided.

In one embodiment the receptacle into which the harvested cells are transferred is a 600 ml bag, sometimes referred to in the field as a "transfer pack".

In one embodiment after harvesting the cells are washed, for example with a solution comprising human serum albumin, saline or similar.

In one embodiment the cells are washed manually.

In one embodiment the cells are washed employing an automated system, for example a Sepax® system available from Biosafe.

In one embodiment, for example after washing, the cells are counted.

In one embodiment, for example after counting, a therapeutic amount of cells (i.e. one or more doses of cells) is selected.

In one aspect the harvested cells are enclosed into a suitable container, for example an infusion bag, optionally along with one or more pharmaceutically acceptable preservatives or excipients, for storage.

Suitable excipients include DMSO, for example 10% DMSO.

In one embodiment the container is transported to the location of a patient.

In embodiment the content of the container is administered to a patient parenterally, particularly intravenously.

In one aspect the invention relates to equine training equipment substantially as defined herein.

In the context of this specification "comprising" is to be interpreted as "including".

Aspects of the invention comprising certain elements are also intended to extend to alternative embodiments "consisting" or "consisting essentially" of the relevant elements.

We claim:

1. A closed system suitable for the aseptic culture of therapeutic cells comprising:
   (i) a vessel comprising:
      a gas permeable portion suitable for supporting cell growth and allowing delivery of gases to the cells during culturing, and
      at least one wall adjoined to a base,
      wherein said vessel defines an internal volume for containing a requisite volume of medium to support a cell culture,
   (ii) a lid
   (iii) a vent in the lid comprising a conduit defining an interior orifice and an exterior orifice distal therefrom in fluid communication with each other which allows balancing of pressure during filling the vessel by allowing gases to exit and during the cell-emptying process allows gases to enter the interior volume,
   wherein the conduit extends from the exterior of the closed system through the lid and extends into the internal volume of the vessel and terminates therein with the interior orifice, and
   wherein the interior orifice is arranged not to contact the medium in the vessel for all orientations of the vessel including when the system is inverted, wherein the system is emptied under gravity, or wherein the interior orifice is covered with a liquid impermeable membrane or a liquid non-return valve, and
   wherein the exterior orifice of the vent conduit is attached to a sterile filter, and
   (iv) a port or ports arranged to provide aseptic introduction of fluids and cells into the vessel, an exit port located on the lid for fluids to exit the system without exposing the system to the external environment which allows cells grown therein to exit the system under gravity when the system is orientated to put the cells in fluid communication with the exit port;
   wherein the vent and said exit port are co-located in the lid; and
   wherein the vent is located centrally on the lid and the exit port is located to the side of the lid,
   wherein said vent conduit extends further into the interior orifice than said exit port does.

2. A system according to claim 1, wherein the vessel is unitary.

3. A system according to claim 2, wherein part of the vessel is arranged to funnel cells to the exit port when the vessel is in an appropriate orientation.

4. A system according to claim 1, wherein the exit port extends 0.15 mm or less into the internal volume.

5. A system according to claim 1, wherein the conduit of the vent extends between 5 and 35 mm into the internal volume of the vessel.

6. A system according to claim 5, wherein the conduit of the vent extends 30 mm from the lid into the internal volume of the vessel.

7. A system according to claim 1, wherein said vent and said port or ports are located opposing the base.

8. A system according to claim 1, wherein the system is arranged to provide aseptic emptying under gravity.

9. A system according to claim 1, wherein the interior orifice is arranged not to contact the medium in the vessel when the system is emptied under gravity by inversion of the system.

10. A system according to claim 1, wherein the interior orifice of the vent is covered with a liquid impermeable membrane or a liquid non-return valve.

11. A system according to claim 1, wherein the system is emptied under gravity by changing the orientation of the system by more than 90 degrees.

12. A system according to claim 1, wherein the conduit of the vent extends to approximately the midpoint of internal volume of the vessel.

13. A system according to claim 1, wherein one port is an entrance and also an exit port.

14. A system according to claim 1, wherein the system comprises a second entrance port to provide aseptic introduction of fluids and cells into the vessel.

15. A method for aseptic culture of therapeutic cells comprising the steps of
   a. aseptically adding to a closed system defined in claim 1 a cell population for culturing
   b. aseptically adding to said system a nutrient of nutrients for culturing the cells, wherein step a may be performed before, after or concomitant with step b,
   c. culturing the cells to expand the target T cell population, and
   d. aseptically harvesting the cells into a suitable container.

16. A method according to claim 15, which comprises the further step of washing the expanded cell population after harvesting.

17. A method according to claim 15, which comprises a further step of counting the expanded cell population after harvesting.

18. A method according to claim 16, which comprises a further step of separating a therapeutic dose of the cells into a suitable container.

19. A method according to claim 15, wherein an excipient such as DMSO is added to the harvested cells.

20. A closed system suitable for the aseptic culture of therapeutic cells comprising:
   (i) a vessel comprising:
      a gas permeable portion suitable for supporting cell growth and allowing delivery of gases to the cells during culturing, and
      at least one wall adjoined to a base,
      wherein said vessel defines an internal volume for containing a requisite volume of medium to support a cell culture,
   (ii) a lid
   (iii) a vent in the lid comprising a conduit defining an interior orifice and an exterior orifice distal therefrom in fluid communication with each other which allows balancing of pressure during filling the vessel by allowing gases to exit and during the cell-emptying process allows gases to enter the interior volume,
      wherein the conduit extends from the exterior of the closed system through the lid and extends into the internal volume of the vessel and terminates therein with the interior orifice, and wherein the interior orifice is arranged so that when the volume of medium is from 10% to 50% of the interior volume of the vessel, for all orientations of the vessel, the medium does not block the vent during cell culturing and removal including when the system is inverted, wherein the system is emptied under gravity, and
   wherein the exterior orifice of the vent conduit is attached to a sterile filter, and
   (iv) a port or ports arranged to provide aseptic introduction of fluids and cells into the vessel, an exit port for fluids to exit the system without exposing the system to the external environment which allows cells grown therein to exit the system under gravity when the system is orientated to put the cells in fluid communication with the exit port;
   wherein the vent and said exit port are co-located in the lid; and
   wherein the vent is located centrally on the lid and said exit port is located to the side of the lid,
   wherein said vent conduit extends further into the interior orifice than said exit port does.

21. A system according to claim 20, wherein the interior orifice of the vent is covered with a liquid impermeable membrane or a liquid non-return valve.

* * * * *